United States Patent [19]

Alvarez et al.

[11] 4,402,982

[45] Sep. 6, 1983

[54] ANTIHYPERTENSION TREATMENT AND COMPOSITION THEREFOR

[75] Inventors: Jose A. A. Alvarez, Carpatos, Mexico; Ralph B. Thompson, Oak Brook, Ill.

[73] Assignee: T & R Chemicals, Inc., Clint, Tex.

[21] Appl. No.: 337,104

[22] Filed: Jan. 5, 1982

[51] Int. Cl.$^3$ .................... A61K 31/14; A61K 31/095
[52] U.S. Cl. .................................... 424/329; 424/162; 424/325; 424/335
[58] Field of Search ..................... 424/162, 248.5, 180, 424/267, 315, 325, 329, 335

[56] References Cited

U.S. PATENT DOCUMENTS

| | | | |
|---|---|---|---|
| 2,367,302 | 1/1945 | Moore . | |
| 3,836,639 | 9/1974 | Teler | 424/101 |
| 3,906,109 | 9/1975 | Roehm | 424/325 |
| 4,327,083 | 4/1982 | Alvarez | 424/162 |

OTHER PUBLICATIONS

Chao, Thrombos. Haemostas (Stuttg) vol. 35, 1976, pp. 717-736.
Shulman, Chem. Abs. vol. 47, 1953, p. 9386.
Gunnison, Fd. Cosmet. Toxicol. vol. 19, 1981, pp. 667-682.
Elias, Abstract of Thromb. Diath. Haemorrh, vol. 18 (3-4) 1967, pp. 499-509.
Torda, Abs. of Anaesth. Intens. Care, 1, 293, (1973).
Bourbon, Abs. of J. Eur. Toxicol. vol. 4, No. 3, pp. 205-207 (1971).
Chem Abs. 9th Coll. Index, p. 37336CS, vol. 82, Ab No. 107247f (1975).
Kikugawa J. Pharm Sci, vol. 61, 1972 pp. 1904-1907.
Rost, "Comparative Invst. of the Pharmacol. Effects of Organically Bonded Sulfurous Acids and of Neutral Sodium Sulfite" in Arb. A. D. Kaiserlicher Gesundheitsamte, vol. 21, 1904, p. 312.

*Primary Examiner*—Anna P. Fagelson
*Attorney, Agent, or Firm*—Cushman, Darby & Cushman

[57] ABSTRACT

The treatment of mammals with organic quaternary ammonium alkali metals, alkaline sulfites and bisulfites suffering from hypertension is described.

7 Claims, No Drawings

ANTIHYPERTENSION TREATMENT AND COMPOSITION THEREFOR

BACKGROUND OF THE INVENTION

Jose Antonio Arias Alvarez has previously discovered that inorganic salts of sulfurous acid (especially sodium bisulfite) are antihypertensive agents; see U.S. Pat. No. 4,327,083 issued Apr. 27, 1982.

Sodium bisulfite (usually shown by formula to be $NaHSO_3$) has heretofore been used for many commercial purposes, such as a preservative for prevention of the deterioration of liquid systems, such as food stuffs and of pharmaceutical solids, and has also been used medically both externally, such as for treatment of parasitic skin diseases, and internally such as for a gastrointestinal antiseptic. So far as now known, sodium bisulfite has never previously been used by man for the treatment of hypertension.

The solid sodium bisulfite of commerce reportedly consists chiefly of sodium metabisulfite, $Na_2S_2O_5$, and sodium bisulfite, and, for purposes of this invention, such is believed to possess the same properties as (and to be equivalent to) sodium bisulfite when dissolved in aqueous solution.

BRIEF SUMMARY OF THE INVENTION

There has now been discovered a class of organic agents, the members of which when introduced by ingestion, injection, absorption, or otherwise into a mammal (including man), produce avoidance, amelioration and/or improvement of a hypertensive condition in mammals and man when used in an antihypertensively effective amount as taught herein.

The active antihypertensive agents of the present invention are organic quaternary salts of sulfurous acid which display antihypertensive activity.

One class of antithrombotic agents of the present invention is characterized by the formula:

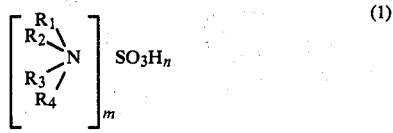

where:
- $R_1$, $R_2$ $R_3$, and $R_4$ are each an independently selected lower alkyl radicals, and
- m and n are integers, the sum of m and n is 2, and n is either 0 or 1.

Another class of such active agents of the present invention is characterized by the formula:

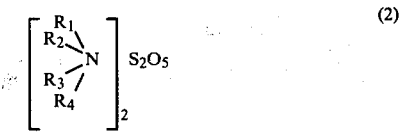

wherein, in each such formula $R_1$, $R_2$, $R_3$ and $R_4$ have their above specified respective meanings.

Presently preferred such compounds are bisulfite compounds, examples of which include: tetramethyl ammonium bisulfite, tetraethyl ammonium bisulfite, tetrabutyl ammonium bisulfite, trimethyl ethyl ammonium bisulfite, tetramethyl ammonium metabisulfite, and the like. Tetra (lower alkyl) ammonium sulfites are also active agents, however.

The term "lower" as used herein has reference to a radical containing less than 6 carbon atoms each.

In one aspect, the present invention is directed to the use of certain organic quaternary amine bisulfite and sulfite salt compounds as antihypertensive agents in human medicine.

In another aspect, the present invention is directed to a method for control of, and/or prevention of, hypertension in man by oral ingestion and/or injection of a pharmacologically effective amount of organic quaternary bisulfites and/or sulfite compound(s) within the scope of the active agents of this invention.

In another aspect, the present invention leads to symptomatic and objective improvement in a cardiovascular disease condition, such as hypertension in man. By the term "symptomatic improvement", as used herein, reference is had to an improvement in a patient's subjective symptoms as reported by that patient. By the term "objective improvement", as used herein, reference is had to a measurable and objective change in the patient's condition (e.g. blood pressure), from an initial (at the start of treatment) to a subsequent (during or after treatment) condition.

Naturally, an active antihypertensive agent of this invention is used, if at all in a mammal, at a pharmaceuticaly effective dose rate, that is, at a dose rate which is below the level of toxicity or of production of undesired side effects. Because of biological complexities, the complete biological effects of the active agents of this invention are not now known.

Other and further aspects, objects, purposes, advantages, aims, utilities, features, and the like will be apparent to those skilled in the art from a reading of the present specification.

DETAILED DESCRIPTION

More particularly, this invention concerns a process for treating a human to control, ameliorate, or prevent a cardiovascular disease such as hypertension wherein there is introduced, preferably orally, into such a human a pharmaceutically effective amount of an active agent of this invention as defined above (preferably a bisulfite).

In one preferred mode of using this invention, an aqueous solution of from about 1 to 15% by weight active agent is prepared. Then such solution is orally consumed by a human, for example, in the form of drops, at a total (or accumulated) dose rate ranging from 0.2 to 20 mg per each kilogram of body weight per day, more particularly in the form of from two to four spaced doses per day, each such dose being preferably taken around meal time.

Symptomatic and/or objective improvement in a patient's hypertensive condition even at relatively low dosage rates may occur within two weeks to four months of such a continuous oral usage of active agent in accord with these teachings of this invention.

Such dilute active agent solutions can be used before, during, or after the onset of a cardiovascular disease with beneficial resuls. Even when used on patients who might be considered terminally affected by such condition, beneficial results are observable.

It is believed that larger and/or smaller such doses can be used without departing from the spirit and scope of the present discovery. One dose rate, for example, which has usually been found to be effective for man varies from about 0.2 to 75 mgm per day per average human adult patient (e.g. about 70 kg) of active agent taken orally as dilute aqueous solution of from about 1 to 5 percent by weight in distilled water and ingested before, during or after each of the daily meals, such as breakfast, lunch, and dinner. Presently, a preferred dose rate for a patient using a self-administered dilute aqueous system comprises one in the range from about 1.0 to 20 mgm per kg of body weight per day taken in the form of at least two spaced oral doses (using such an aqueous solution as described herein). The water used in such a solution is preferably purified (e.g. filtered, deionized, distilled or the like). After preparation, such a solution is preferably stored in a closed container.

Such an aqueous solution can be directly consumed by a patient as drops (e.g. from about 5 to 20 drops per meal, depending upon dose rate for an individual patient), or as a capsule, or the like, as desired.

A subjective improvement in atherosclerosis may be observable by some patients who have been dosed as described above. It may be that use of this invention exerts a favorable influence on blood lipids, such as a fall in total cholesterol.

One important advantage of the present invention is the circumstance that the indicated desirable results may be achieved with little or no apparent side effects surprisingly. For example, no change in a normal excretion rate of such metallic ions as sodium, potassium, magnesium, or calcium through urine appears to be associated with the use of active agents of this invention, contrary to normal experience with conventional diuretic agents which are used to lower blood pressure.

The active agents of this invention can be administered by any convenient or appropriate procedure. For example, injection by intravenous, intraperitoneal, intramuscular or subcutaneous administration of such a dilute aqueous solution as described above may afford a more rapid reduction in blood pressure than is observable from oral administration for reasons which are not presently known. Suppositories containing active agents can be used for absorption.

The active agents of the present invention can be formulated in any desired manner for administration. For example, conventional excipients, extenders, compounding agents and the like can be blended with powdered active agents and the resulting blends can be tableted, pilled, pelletized, or the like and the used as solid oral dosage forms. Conveniently, individual dosage units, in whatever form prepared or compounded, can range from about 50 to 500 milligrams (mg) each.

Per diem (24 hour day) dose rates for active agents of this invention for mammals (including man) are believed to range from about 0.2 to 50 mg per kg of body weight, with doses ranging from about 1 to 20 mg per kg being more general, convenient and typical for practical, safe administration. Larger and smaller dose rates can be employed without departing from the spirit and scope of this invention.

Compounds (active agents) of this invention are conveniently prepared by preparing an aqueous solution preferably using a purified or distilled water of a corresponding lower tetraalkyl ammonium hydroxide compound wherein such compound is present at a specified or calculated concentration, such as 10 weight percent. Then, through this solution is bubbled $SO_2$ gas until the resulting solution increases in weight to an extent sufficient to produce a weight corresponding to the desired sulfite or bisulfite salt. For example, to prepare a product solution which is substantially a bisulfite salt, twice as much weight increase is needed compared to the corresponding sulfite salt. If the starting tetraalkyl ammonium hydroxide is not fully soluble (or fully in a dissolved form) at the start of the sulfur dioxide gas addition (but is partially only dispersed or suspended in the aqueous phase), it becomes completely dissolved as $SO_2$ addition continues. By an alternative synthetic procedure an ion exchange resin in the sulfite form could be used, if desired. Some of the production solutions made from various starting corresponding quaternary compounds can be, after preparation, subsequently evaporated to dry solid form, such as the tetramethyl ammonium metabisulfite; others appear to exist only in solution form, such as the tetramethyl ammonium bisulfite.

The water used in a solution, of an active agent, is preferably purified (e.g., filtered, deionized, distilled, or the like). After preparation, such a solution is preferably stored in a closed container to reduce oxidation.

Such an aqueous solution can be directly used in accordance with the teachings of this invention, which even such a solution can be dispensed dropwise, or such a solution can be encapsulated, or the like, and used as measured dosage units, as desired. For example, an aqueous solution containing 5 weight percent of active agent can be injected into a patient or it can be directly consumed by a patient as drops (e.g., from about 5 to 9 drops per meal for each of the two or three meals eaten by such patient per day, depending upon an individual patient's body weight, or the like).

EMBODIMENTS

The present invention is further illustrated by reference to the following case histories. Those skilled in the art will appreciate that other and further embodiments are obvious and within the spirit and scope of this invention from the teachings of these present examples taken with the accompanying specification.

PREPARATION OF ACTIVE AGENTS

Solution A Preparation

A 10 weight percent aqueous solution of tetramethyl ammonium bisulfite is prepared by bubbling $SO_2$ through a solution of tetramethyl ammonium hydroxide to form the desired aqueous product solution.

Solution B Preparation

Using the procedure of Solution A, a 10 weight percent aqueous solution of a tetraethyl ammonium bisulfite is prepared from tetraethyl ammonium hydroxide.

Solution C Preparation

Using the procedure of Solution A, a 10 weight percent aqueous solution of trimethyl ethyl ammonium bisulfite is prepared from trimethyl ethyl ammonium hydroxide.

Solution D Preparation

Using the procedure of Solution A, a 5 weight percent aqueous solution of tetrabutyl ammonium bisulfite is prepared from tetrabutyl ammonium hydroxide.

Solution E Preparation

A sample of this tetramethyl ammonium bisulfite (Solution A) is evaporated in a Buchi rotary evaporator under vacuum to dryness. When the water is all removed, an oil bath heated to 130° C. is applied to the flask containing the solid and heating under vacuum is continued for 4 more hours thereby removing water from this bisulfite to produce the metabisulfite from the starting bisulfite.

Solution F Preparation

A 5 weight percent aqueous solution of tetramethyl ammonium sulfite is prepared by bubbling $SO_2$ through a solution of tetramethyl ammonium hydroxide to form the desired aqueous product solution. One half as much $SO_2$ is consumed compared to Solution A preparation.

I claim:

1. A method of treating hypertension in a human suffering from said condition comprising introducing into said human an antihypertensively effective amount of at least one compound of the formulas:

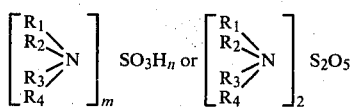

wherein:
R$_1$, R$_2$, R$_3$, R$_4$ are each independently lower alkyl groups, and
m and n are each an integer whose combined sum is equal to 2, and m is 0 or 1.

2. The method of claim 1 in which the amount administered is from about 0.2 to about 75 mg per kg of body weight per day.

3. The method of claim 2 in which the amount administered is from about 0.2 to about 20 mg per kg of body weight per day.

4. The method of claim 1 in which said agent is administered in divided doses of at least two doses per day.

5. A pharmaceutical composition for the treatment of hypertension consisting essentially of an antihypertensive-effective amount of a compound of the formula:

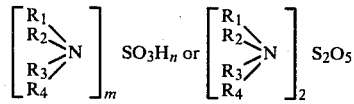

wherein:
R$_1$, R$_2$, R$_3$, R$_4$ are each independently lower alkyl groups, and
m and n are each an integer whose combined sum is equal to 2, and m is 0 or 1,
together with a pharmaceutically acceptable carrier or diluent.

6. The pharmaceutical composition of claim 5 in which from about 1 to about 15 weight percent of said compound is dissolved in an aqueous solution.

7. A pharmaceutical composition adapted for oral administration in the treatment of hypertension containing about 50 to about 500 mg of the compound of claim 5 together with a pharmaceutically acceptable carrier or diluent.

* * * * *